(12) United States Patent
Cromack et al.

(10) Patent No.: US 9,039,748 B2
(45) Date of Patent: May 26, 2015

(54) METHOD OF SECURING A MEDICAL DEVICE ONTO A BALLOON AND SYSTEM THEREOF

(75) Inventors: Keith R. Cromack, Gurnee, IL (US); Donald Verlee, Livertyville, IL (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 956 days.

(21) Appl. No.: 12/419,617

(22) Filed: Apr. 7, 2009

(65) Prior Publication Data

US 2010/0069946 A1 Mar. 18, 2010

Related U.S. Application Data

(60) Provisional application No. 61/042,973, filed on Apr. 7, 2008.

(51) Int. Cl.

| | |
|---|---|
| *A61F 2/06* | (2013.01) |
| *A61L 31/16* | (2006.01) |
| *A61L 29/08* | (2006.01) |
| *B29C 35/02* | (2006.01) |
| *B29C 65/48* | (2006.01) |
| *B29C 65/52* | (2006.01) |
| *B29K 23/00* | (2006.01) |
| *B29K 27/12* | (2006.01) |
| *B29K 67/00* | (2006.01) |
| *B29K 71/00* | (2006.01) |
| *B29K 75/00* | (2006.01) |
| *B29K 77/00* | (2006.01) |
| *B29K 79/00* | (2006.01) |
| *B29K 83/00* | (2006.01) |
| *B29K 101/10* | (2006.01) |
| *B29K 101/12* | (2006.01) |
| *B29K 305/00* | (2006.01) |
| *B29L 23/00* | (2006.01) |
| *B29L 31/00* | (2006.01) |

(52) U.S. Cl.
CPC .............. *A61L 31/16* (2013.01); *A61L 29/085* (2013.01); *A61L 2300/00* (2013.01); *B29C 35/02* (2013.01); *B29C 65/4895* (2013.01); *B29C 65/52* (2013.01); *B29K 2023/00* (2013.01); *B29K 2023/16* (2013.01); *B29K 2027/12* (2013.01); *B29K 2067/00* (2013.01); *B29K 2067/006* (2013.01); *B29K 2067/046* (2013.01); *B29K 2071/00* (2013.01); *B29K 2075/00* (2013.01); *B29K 2077/00* (2013.01); *B29K 2079/08* (2013.01); *B29K 2083/00* (2013.01); *B29K 2101/10* (2013.01); *B29K 2101/12* (2013.01); *B29K 2305/00* (2013.01); *B29L 2023/007* (2013.01); *B29L 2031/7542* (2013.01); *B29C 65/4835* (2013.01); *B29C 65/483* (2013.01)

(58) Field of Classification Search
USPC .......................... 606/191–200; 623/1.11, 1.23
See application file for complete search history.

(56) References Cited

U.S. PATENT DOCUMENTS

| | | | |
|---|---|---|---|
| 4,260,873 A * | 4/1981 | Simmonds | .................... 392/404 |
| 4,580,568 A | 4/1986 | Gianturco | |
| 4,733,665 A | 3/1988 | Palmaz | |
| 4,963,313 A | 10/1990 | Noddin | |
| 5,091,205 A * | 2/1992 | Fan | ............................... 427/2.28 |
| 5,304,121 A * | 4/1994 | Sahatjian | ...................... 604/509 |
| 5,714,110 A | 2/1998 | Wang | |
| 5,755,771 A | 5/1998 | Penn et al. | |
| 6,033,434 A | 3/2000 | Borghi | |
| 6,063,092 A | 5/2000 | Shin | |
| 6,106,548 A | 8/2000 | Roubin | |
| 6,120,436 A | 9/2000 | Anderson et al. | |
| 6,890,339 B2 * | 5/2005 | Sahatjian et al. | ............. 606/194 |
| 7,527,632 B2 * | 5/2009 | Houghton et al. | ............ 606/108 |

FOREIGN PATENT DOCUMENTS

WO   WO 2004017868 A1 *   3/2004   ................ A61F 2/06

* cited by examiner

*Primary Examiner* — Darwin Erezo
*Assistant Examiner* — Lindsey Bachman
(74) *Attorney, Agent, or Firm* — Baker Botts, LLP

(57) ABSTRACT

A method for securing an implantable medical device onto a balloon which includes applying a coating, which includes a film-forming polymer and at least one solvent, to the outer surface of the balloon. The solvents can include alcohol, water, ether and combinations thereof. The film-forming polymer can include a zwitterionic polymer, such as, for example a phosphorylcholine polymer. The coating can be applied to the entire balloon surface or a portion of the surface. The implantable medical device is then positioned on the outer surface of the balloon and secured. The film-forming polymer is then allowed to cure in order to define an adhesive layer between an inner surface of the implantable medical device and the outer surface of the balloon. This method prevents or reduces the leaching or redistribution of any therapeutic agents dispersed within or on the surface of the implantable medical device.

22 Claims, No Drawings

METHOD OF SECURING A MEDICAL DEVICE ONTO A BALLOON AND SYSTEM THEREOF

CROSS-REFERENCE TO RELATED APPLICATIONS

This application claims the benefit of U.S. Provisional Application Ser. No. 61/042,973 filed on Apr. 7, 2008.

BACKGROUND

1. Field of the Invention

The invention relates to a method of securing an implantable medical device onto a balloon. Particularly, the invention relates to a method of securing an implantable medial device by coating the outer surface of the balloon with a film-forming polymer and subsequently securing the implantable medical device to the surface of the balloon.

2. Description of Related Art

Cardiovascular disease is prevalent in the United States and in other parts of the world. One manifestation of cardiovascular disease is atherosclerosis, which is the buildup of plaque (or fatty deposits) on the walls of blood vessels, such as coronary arteries. This buildup of plaque can grow large enough to reduce blood flow through the blood vessel. Serious damage results when an area of plaque ruptures and forms a clot, which travels to another part of the body. If the blood vessels that feed the heart are blocked, a heart attack results. If the blood vessels to the brain are blocked, a stroke results. Thus, atherosclerosis can be fatal for some people.

Typically, atherosclerosis is treated by percutaneous transluminal coronary angioplasty (PTCA). This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

While PTCA is widely used, it suffers from two unique problems. First, the blood vessel may suffer acute occlusion immediately after or within the initial hours after the dilation procedure. Second, the re-narrowing of an artery or other blood vessel after an initially successful angioplasty sometimes results. This blood vessel re-narrowing is commonly referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce the restenosis rate of angioplasty alone and to strengthen the dilated area, physicians typically implant a tubular endoprosthesis, generally called a stent, inside the vasculature at the site of the lesion or blocked segment. Stents may also be used to repair vessels having an intimal flap or dissection or to generally strengthen a weakened section of a vessel or to maintain its patency. A typical stent-delivery system for balloon expandable stents is characterized by a catheter equipped with a dilation balloon and a stent mounted on the balloon, otherwise known as a stent delivery system. In such a system, the stent is slipped over a folded catheter balloon and crimped in place. Additionally, the stent or implantable medical device may be loaded with one or more therapeutic agents, such as antiproliferatives, for delivery to the target lesion. The stent delivery device enters the vasculature of a patient and travels through a tortuous path to the site of the lesion. The physician positions the stent across the lesion and deploys the stent so that the stent forces the plaque against the inside wall of the blood vessel (or lumen) and maintains its expanded configuration so that the patency of the blood vessel is maintained.

A fairly common problem with stent deployment, however, is slippage and early unintentional release of the stent. The stent may pop off the balloon during inflation, or slip backward off the balloon during steering to the intended site of release. This condition most often occurs in small or heavily occluded arteries where contact with either the arterial wall or the lesion to be treated forces the stent off of the catheter balloon. Additionally, passage of the exposed stent through any valves may cause the stent to be dislodged from the balloon. If the stent is dislodged from or moved relative to the balloon, the system will not correctly implant the stent into body lumen. Alternatively, if a stent slips off of the balloon, or if it slips forward off the balloon in a partially expanded condition, the steps necessary to remove the stent can severely damage an artery, and may even require grossly invasive surgery to remove the stent.

Different methods have been attempted to maintain the position of the stent on the expandable member. One such method involves a protective sheath surrounding the catheter and stent assembly, which is retracted prior to inflation of the expandable member. The use of the sheath, however, increases the profile of the catheter assembly which must traverse narrow vessels. Other methods include applying dissolvable bands to the stent surface to hold the stent in place. The bands, however, also add significantly to the outer diameter of the stent assembly and leave exposed sharp and irregular contours of the stent assembly.

Other methods to increase stent retention include providing protrusions on the balloon or on the catheter near the balloon, the protrusions having shoulders above and/or below the stent location which bears against the stent when it is subjected to an axial force. Alternatively, protrusions may be provided on the external surface of the balloon, or on a sleeve located between the stent and the balloon, which protrude into the holes through the wall of the stent. However, the procedures used to make such balloons tend to lead to weakening of the balloon wall, an increase in the pressure required to inflate the balloon, and/or require additional manufacturing steps and steps for careful positioning of the stent upon the balloon.

Other methods include coating the exterior surface of the stent delivery device with a film-forming polymer coating, which includes a solvent. However, the solvent that is present in the coating tends to remove or redistribute any drugs that have been loaded on the stent.

Accordingly, it would be beneficial to provide a catheter balloon having improved stent retention without inhibiting balloon or catheter function. Particularly, the stent mounting procedure must not damage a drug or drug delivery matrix on the stent delivery system.

SUMMARY

To achieve these and other advantages, the invention includes a method for securing an implantable medical device onto a balloon which provides advantages such as reduced drug leaching. The implantable medical device can be intended for implantation in an artery or a tear duct. The medical device is, for example and not limitation, a stent, graft or stent-graft structure or other tubular member adapted for delivery into an anatomical lumen.

The method for securing the implantable medical device onto the balloon includes applying a coating, which includes a film-forming polymer and at least one solvent, to the outer surface of the balloon. The solvents can include alcohol, water, ether and combinations thereof. The film-forming polymer can include a zwitterionic polymer, such as, for example a phosphorylcholine polymer. The coating can be applied to the entire balloon surface or a portion of the balloon surface. The implantable medical device is then positioned on the outer surface of the balloon and secured. The film-forming polymer is then allowed to cure in order to define an adhesive layer between the inner surface of the implantable medical device and the outer surface of the balloon.

In one embodiment, the implantable medical device can be positioned on the surface of the balloon before the coating is dried. In this regard, the balloon is considered as having a tacky or slightly adhesive surface and the implantable medical device is positioned on the outer surface of the tacky balloon. Alternatively, the implantable medical device can be positioned on the surface of the balloon after the coating is dried. Preferably, the coating is not allowed to cross-link or cure prior to the positioning of the implantable medical device on the balloon surface.

In another embodiment, a method for securing the implantable medical device to the balloon surface includes applying a coating, which includes a film-forming polymer and at least one solvent, to a portion or the entire outer surface of the balloon. The coating is then allowed to dry and the implantable medical device is subsequently positioned on the outer surface of the balloon and secured, such as by crimping. Thereafter, a solvent is applied to the surface of the implantable medical device/balloon assembly in order to dissolve the layer of film-forming polymer between the inner surface of the implantable medical device and the outer surface of the balloon. Preferably, the solvent is applied as a vapor or fine liquid mist. The film-forming polymer coating is then allowed to cure to define an adhesive layer between an inner surface of the implantable medical device and the outer surface of the balloon.

In another embodiment, a method for securing the implantable medical device to the balloon surface includes applying a coating, which includes a film-forming polymer and at least one solvent, to a portion or the entire outer surface of the balloon. The coating is then allowed to dry and the implantable medical device is subsequently positioned on the outer surface of the balloon and secured, such as by crimping. Thereafter, the implantable medical device/balloon assembly is heated in order to dissolve the layer of film-forming polymer between the inner surface of the implantable medical device and the outer surface of the balloon.

Preferably, and in one embodiment, at least one therapeutic agent is dispersed on the implantable medical device. For example, the therapeutic agent can be coated on the surface of the implantable medical device by various coating techniques including, but not limited to, spraying, dipping or jetting. Alternatively, the implantable medical device can be formed from a substance containing the therapeutic agent. The implantable medical device may also have reservoirs or pores containing the therapeutic agent. The therapeutic agent can be selected from, but not limited to, anti-proliferative, anti-inflammatory, antineoplastic, antiplatelet, anti-coagulant, anti-fibrin, antithrombonic, antimitotic, antibiotic, antiallergic and antioxidant compounds.

In accordance with the invention, the outer surface of the implantable medical device is substantially free of the film-forming polymer. Therefore, leaching of the therapeutic agent from the implantable medical device is prevented or reduced.

In accordance with another embodiment, the invention includes a medical device system including a balloon having a film-forming polymer coating on a portion of the outer surface of the balloon and an implantable medical device secured to the surface of the balloon. The film-forming polymer coating on the surface of the balloon defines an adhesive layer between the inner surface of the implantable medical device and the balloon.

It is to be understood that both the foregoing general description and the following detailed description are exemplary and are intended to provide further explanation of the invention claimed.

DETAILED DESCRIPTION OF THE EMBODIMENT

While this invention may be embodied in many different forms, reference will now be made in detail to the specific embodiments of the invention. This description is an exemplification of the principles of the invention and is not intended to limit the invention to the particular embodiments illustrated.

The invention includes a method for securing an implantable medical device onto the surface of a balloon catheter. The method provides for improved retention of the implantable medical device and improved device delivery functions. Particularly, the implantable medical device mounting procedure of the present invention prevents or reduces the leaching or redistribution of any therapeutic agents dispersed within or on the surface of the implantable medical device.

The method for securing the implantable medical device onto the balloon includes applying a coating, which includes a film-forming polymer and at least one solvent, to the outer surface of the balloon. The coating can be applied to the entire balloon surface or a portion of the balloon surface. The implantable medical device is then positioned on the outer surface of the balloon and secured. The film-forming polymer is then allowed to cure in order to define an adhesive layer between an inner surface of the implantable medical device and the outer surface of the balloon. Curing generally comprises removal of the solvent, for instance by evaporation under raised temperature and/or reduced pressure.

In one embodiment, the curing of the film-forming polymer also comprises crosslinking of a crosslinkable polymer in the coating composition. Crosslinking may be carried out before, during and/or after solvent removal. Crosslinking of a polymer which includes crosslinkable groups involves subjecting the polymer to conditions under which the crosslinkable groups react to form inter- and intra molecular bonds. Such conditions generally involve heating the polymer, exposing it to incident actinic radiation and/or to moisture or gaseous crosslinking agents. Such agents may include ethylene oxide.

The coating used on the surface of the balloon preferably comprises a film-forming polymer and a solvent in which the polymer is dissolved or dispersed. A film-forming polymer is a polymer than can be dissolved in a solvent, melted or otherwise processed to a liquid state where it can be applied to a surface using various application techniques. The film-forming polymer will initially form a liquid film that will subsequently harden to a solid adherent film having a desired thickness and consistency. In most film-formation processes, a liquid coating of relatively low viscosity is applied to a solid substrate and is cured to a sold, high-molecular-weight, polymer-based adherent film possessing the properties desired by the user. For purpose of illustration and not limitation, the film-forming polymer includes a zwitterionic polymer, such as phosphorylcholine linked macromolecules, including a macromolecule containing pendant phosphorylcholine groups including poly(MPC$_w$:LMA$_x$:HPMA$_y$:TSMA$_z$), where MPC is 2-methacryoyloxyethylphosphorylcholine, LMA is lauryl methacrylate, HPMA is hydroxypropyl methacrylate and TSMA is trimethoxysilylpropyl methacrylate, and w, x, y, and z are molar ratios of the monomers used in the feed. These values are typically 23, 47, 25, and 5, respectively, but they are not necessarily the ratios that exist in the finished polymer. Additional film forming polymers include, but are not limited to, celluloses, polysaccharides, amino acids, non-ionic hydrophilics, ionic hydrophilics, acrylates, waxes, hydrophobics or aliphatic polyesters, and any combination thereof. Examples of cellulose compounds include, but are not limited to, hydroxypropyl methyl cellulose, hydroxypropyl cellulose, hydroxyethyl cellulose, cellulose acetate phthalates, hydroxyethylmethyl cellulose, hydroxypropyl methyl cellulose acetate succinate, hydroxypropyl methyl cellulose phthalate, methylcellulose and carboxymethyl cellulose sodium. Examples of polysaccharide compounds include, but are not limited to, heparin, heparin and hydrophobic block copolymer, heparin and benzoyl chloride (counter-ion), dextran, sulfonated dextran, sodium hyaluronate, hyaluronic acid, hyaluronan, chitosan, sodium alginate, sucrose, glycosaminoglycans, pectin, xanthan gum, dextrin, maltodextrin, polydextrose, and carrageenan. Examples of amino acids include, but are not limited to, gelatin and zein. Examples of non-ionic hydrophilic compounds include, but are not limited to, poly(ethylene glycol), polyvinylpyrrolidone, poly(vinyl alcohol), polyethylene oxide and copovidone. Examples of ionic hydrophilic compounds include, but are not limited to, carbopol, low molecular weight chitosan and polystyrene sulfonate. Examples of acrylates include, but are not limited to, poly(acrylic acid), poly(acrylamide) and polymethacrylates. Examples of waxes include, but are not limited to, paraffin, plasticizers, carnauba wax, white wax, yellow wax and microcrystalline wax. Examples of hydrophobics of aliphatic polyesters include, but are not limited to, poly(L-lactide), poly(D,L-lactide-co-glycolide), poly(DL lactide), poly(glycolide), polycaprolactone and poly(lactide-co-caprolactone).

The phosphorylcholine-linked polymer can include one or more trimethoxysilane functional groups. It is believed that the trimethoxysilane functional group allows crosslinking of the polymer. Alternatively, a linear phosphorylcholine polymer can be used. The film forming polymer is preferably biodegradable or bioresorbable.

The film-forming polymer is dissolved or dispersed in at least one solvent. For purpose of illustration and not limitation, examples of suitable solvents include water, aliphatic hydrocarbons, aromatic hydrocarbons, alcohols, ketones, ethers, dimethyl sulfoxide, tetrahydrofuran, dihydrofuran, dimethylacetamide, acetates, and combinations thereof. In another embodiment, the coating composition includes a mixture of two or more solvents. For example, the solvent mixture can consist of ethanol, optionally with glycol, mixed with water or with alkane.

Generally, the method for securing the implantable medical device onto the balloon includes applying a coating, which includes a film-forming polymer and at least one solvent, to the outer surface of the balloon. In one embodiment, the coating includes 1 to 50 percent by weight of a film-forming polymer in an appropriate solvent. Preferably, the coating includes 1 to 50 percent by weight of phosphorylcholine polymer in solvent, more preferably the coating includes 1 to 10 percent by weight of phosphorylcholine polymer in solvent.

The coating is applied in an adequate thickness to provide enough surface area and adequate retention of the implantable medical device on the balloon surface. In one embodiment, the coating thickness is in the range of 0.05 to 10 microns, more preferably from 0.5 to 2 microns. The coating thickness may be adjusted as desired by controlling the concentration of the film-forming polymer, by selecting suitable coating conditions, for instance in terms of temperature, number of coatings applies or by selecting suitable drying conditions.

The coating can be applied to the entire balloon surface or a portion of the balloon surface. The coating can be applied by various coating techniques including, but not limited to, dip coating and spray coating, as understood in the art. The implantable medical device is then positioned on the outer surface of the balloon and secured. In one embodiment, the implantable medical device is secured to balloon surface by placing the medical device/balloon combination into a crimper and compressing the stent onto the balloon surface by crimping. Thereafter, the film-forming polymer is allowed to cure in order to define an adhesive layer between an inner surface of the implantable medical device and the outer surface of the balloon.

Various embodiments to this general process are discussed herein. In one embodiment, the implantable medical device can be positioned on the surface of the balloon before the coating is dried. In this regard, the balloon is considered as having a tacky or slightly adhesive surface and the implantable medical device is positioned on the outer surface of the tacky balloon. To prevent the film-forming polymer from drying to quickly, thereby ensuring that the surface of the balloon is tacky when the implantable medical device is positioned thereon, the coating solution can contain a second liquid solvent that has a higher boiling point, and therefore a slower drying time, than the first solvent. Therefore, the use of a coating with a two solvent system, one solvent having a higher boiling point than the other, would prevent the film on the balloon from drying to quickly and would allow the coating on the balloon to remain tacky or slightly adhesive.

Additionally, the use of a two solvent system, for example, ethanol-water, would allow the solvent to be adjusted such that the film-forming polymer is soluble enough to coat the balloon surface, but the drug on the implantable medical device is not soluble enough to leach out of the implantable medical device into the adhesive layer during the drying/curing time.

After the medical device is positioned on the tacky balloon it is secured via suitable securing techniques. The implantable medical device is then positioned on the outer surface of the balloon and secured.

Alternatively, the implantable medical device can be positioned on the surface of the balloon after the coating is dried. In this embodiment, a coating which includes a film-forming polymer and at least one solvent, is applied to a portion or to the entire outer surface of the balloon. The coating is then allowed to dry. Preferably, however, the coating is not allowed to cross-link. The implantable medical device is subsequently positioned on the outer surface of the balloon and secured, such as by crimping. Thereafter, a solvent is applied to the surface of the implantable medical device/balloon assembly. Preferably, the solvent is applied as a vapor or fine liquid mist. The liquid mist can wick into the space between the implantable medical device and the balloon to dissolve the layer of film-forming polymer between the inner surface of the implantable medical device and the outer surface of the balloon and create an adhesive layer. Similarly, the vapor can condense on the surface of the implantable medical device and wick into the space between the implantable medical device and the balloon to dissolve the film-forming polymer. In one embodiment, the implantable medial device/balloon assembly can be exposed to a boiling solvent vapor in a vapor polishing apparatus. Vapor polishing techniques can include placing the medial device/balloon assembly into a chamber filled with solvent vapor for a short duration or directing a stream of vapor at the medial device/balloon assembly from an apparatus composed of a container for a suitable solvent, such as methylene chloride, a thermostatically controlled electric heating element for vaporizing the solvent and an open-end guide tube for directing the vaporized solvent to the surface to be polished. Examples of vapor polishing techniques and apparatus are described in U.S. Pat. No. 4,260,873 to Simmonds, the disclosure of which is incorporated in its entirety by reference herein.

Thereafter, the film-forming polymer coating is allowed to cure to define an adhesive layer between an inner surface of the implantable medical device and the outer surface of the balloon. Particularly, the solvent evaporates and the film-forming polymer that remains serves as an adhesive layer.

In another embodiment, the secured balloon/implantable medical device assembly can be heated to define an adhesive layer between the inner surface of the implantable medical device and the outer surface of the balloon. In this embodiment, a coating which includes a film-forming polymer and at least one solvent, is applied to a portion or to the entire outer surface of the balloon. The coating is then allowed to dry. Preferably, however, the coating is not allowed to cross-link. The implantable medical device is subsequently positioned on the outer surface of the balloon and secured, such as by crimping. Thereafter, the implantable medical device/balloon assembly is heated to cure the film-forming polymer coating and dissolve or soften the layer of film-forming polymer between the inner surface of the implantable medical device and the outer surface of the balloon. The heating of the implantable medical device/balloon assembly promotes adhesion or blocking of the implantable medical device on the balloon surface. Suitable techniques known by those skilled in the art can be used for heating implantable medical device/balloon assembly, such as for example heat set blocks. Examples of a heat set and crimping process are described in U.S. Pat. No. 6,063,092 to Shin, the disclosure of which is incorporated in its entirety by reference herein.

Alternatively, a combination of vapor polishing by exposing the implantable medical device/balloon assembly to a boiling solvent vapor heat blocking can be used to promote adhesion of the implantable medical device onto the balloon surface.

In one embodiment, the film-forming polymer is applied only to the surface of the balloon and is cured to define an adhesive layer between the inner surface of the implantable medical device and the outer surface of the balloon. Additionally, the film-forming polymer can also be applied to at least a portion of the inner surface of the implantable medical device. In this regard, curing of the medical device/balloon assembly enables adhesion of the film-forming polymer on the inner surface of the implantable medial device to the film-forming polymer on the outer surface of the balloon.

Preferably, and in one embodiment, at least one therapeutic agent is dispersed on the implantable medical device. For example, the therapeutic agent can be coated on the surface of the implantable medical device by various coating techniques including but not limited to spraying, dipping or jetting. Alternatively, the implantable medical device can be formed from a substance containing the therapeutic agent. The implantable medical device may also have reservoirs or pores containing the therapeutic agent.

The outer surface of the implantable medical device is substantially free of the film-forming polymer. Therefore, the implantable medical device mounting procedure of the present invention prevents or reduces the leaching or redistribution of any therapeutic agents dispersed within or on the surface of the implantable medical device.

The term "implantable medical device" refers broadly to any device suitable for implantation. For purposes of illustration and not limitation, the implantable medical device can be a stent, graft, stent-graft, filter, occlusive device and the like.

In one embodiment, the implantable medical device is a stent. The stent of the invention is a balloon expandable stent having any configuration or pattern, as known to one skilled in the art. The stent body can comprise metal, metal alloy, or polymeric material. Some exemplary materials include Nitinol and stainless steel. Other complimentary materials include cobalt chromium alloy, ceramics and composites. Suitable polymeric materials include thermotropic liquid crystal polymers. The stent can also be fabricated from bioabsorbable or biostable polymers.

The stent can be fabricated utilizing any number of methods known in the art. For example, the stent can be fabricated from a hollow or formed tube that is machined using lasers, electric discharge milling, chemical etching or other known techniques. Alternatively, the stent can be fabricated from a sheet that is rolled into a tubular member, or formed of a wire or filament construction as known in the art. Examples of such fabrication techniques for purpose of illustration include U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, the disclosures of which are incorporated in their entirety by reference herein.

The implantable medical device is not intended to be limited to cardiovascular applications. For example and not limitation, other applications are also intended to be in the scope of the invention including spinal or other orthopedic implants, neurovascular or gastrointestinal implants and the like.

For purpose of illustration and not limitation, the balloon is fabricated from one or more polymers (e.g., a mixture of polymers). For example, the polymers can include one or more thermoplastics and/or thermoset polymers. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers, and silicones. Other examples of thermosets include epoxies and isocyanates. Biocompatible thermosets may also be used. Biocompatible thermosets include, for example, biodegradable polycaprolactone, poly(dimethylsiloxane) containing polyurethanes and ureas, and polysiloxanes. Ultraviolet curable polymers, such as polyimides, can also be used. Other examples of polymers that can be used to fabricated the balloon include polyethylenes, polyethylene ionomers, polyethylene copolymers, polyetheretherketone (PEEK), thermoplastic polyester elastomers (e.g., Hytrel®)), and combinations thereof. The balloon can include multiple layers provided, for example, by coextrusion.

A balloon can be formed using any suitable technique, such as blow molding, film molding, injection molding, and/or extrusion. For example, a polymer tube can be extruded, and can thereafter be stretched and blown to form a balloon. Methods of forming a balloon from a tube are described, for example, in U.S. Pat. No. 6,120,364 to Anderson; U.S. Pat. No. 5,714,110 to Wang; and U.S. Pat. No. 4,963,313 to Noddin, the disclosures of which are incorporated in their entirety by reference herein.

The at least one therapeutic agent may be a variety of therapeutic agents. The term "therapeutic agent" as used herein, refers to any compound, mixture of compounds, or composition of matter consisting of a compound, which produces a therapeutic or useful result. For example and as will be discussed below. The therapeutic agent can be a polymer, a marker, such as a radiopaque dye or particles, or can be a drug, including pharmaceutical agents, or an agent including inorganic or organic drugs without limitation. The therapeutic agent can be in various forms, such as uncharged molecules, components of molecular complexes, pharmacologically acceptable salts such as hydrochloride, hydrobromide, sulfate, laurate, palmitate, phosphate, nitrate, borate, acetate, maleate, tartrate, oleate, and salicylate.

For example and not limitation, the at least one therapeutic agent can include anti-proliferative, anti-inflammmatory, antineoplastic, antiplatelet, anti-coagulant, anti-fibrin, anti-thrombonic, antimitotic, antibiotic, antiallergic and antioxidant compounds. Thus, the therapeutic agent may be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 42-O-(2-hydroxyethyl)rapamycin (everolimus), 42-O-(3-hydroxypropyl)rapamycin, 42-O-(2-hydroxyethyoxy)ethylrapamycin, 42-O-(2-ethoxyethyl)rapamycin, 42-O-tetrazolyl-rapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone, dexamethasone acetate, and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells.

Other therapeutic agents which are currently available or that may be developed in the future for use with implantable medical devices may likewise be used and all are within the scope of this invention.

For example and not limitation, the therapeutic agents effective in preventing restenosis, including those classified into the categories of anti-proliferative agents, anti-platelet agents, anti-inflammatory agents, anti-thrombotic agents, and thrombolytic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

According to the McGraw-Hill Dictionary of Scientific and Technical Terms, Fifth Edition, an analog is "[a] compound whose structure is similar to that of another compound but whose composition differs by one element," and a derivative is "a substance that is made from another substance." These definitions are adopted throughout this document.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpI-IbIIIa or αvβ3, antibodies that block binding to gpIIaIIIb or αvβ3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be anti-inflammatory agent. Non-limiting examples of anti-inflammatory agents include prednisone, dexamethasone, dexamethasone acetate, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, including, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other therapeutic agents include cytotoxic drugs, including, for example, apoptosis inducers, including TGF, and topoisomerase .inhibitors, including, 10-hydroxycamptothecin, irinotecan, and doxorubicin. Other therapeutic agents include drugs that inhibit cell de-differentiation and cytostatic drugs. The at least one therapeutic agent can also include anti-lipaedemic agents, including fenofibrate, matrix metalloproteinase inhibitors, including, for example, batimistat, antagonists of the endothelin-A receptor, including, for example, darusentan, and antagonists of the αvβ3 integrin receptor.

In accordance with another embodiment of the invention, the at least one therapeutic agent can be mixed with a polymer to carry or allow controlled release of the therapeutic agent. The polymer may be in true solution, saturated, or suspended as particles or supersaturated in the beneficial agent. The polymer can be biocompatible, or biodegradable. For purpose of illustration and not limitation, the polymeric material includes polycaprolactone, poly-D,L-lactic acid, poly-L-lactic acid, poly(lactide-co-glycolide), poly(hydroxybutyrate), aliphatic polycarbonates, fibrin, fibrinogen, cellulose, starch, collagen, polyurethane, polyethylene, polyethylene terapthalate, ethylene vinyl acetate, ethylene vinyl alcohol, silicone including polysiloxanes and substituted polysiloxanes, polyethylene oxide, polybutylene terepthalate-co-PEG, PCL-co-PEG, PLA-co-PEG, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and epoxies.

In another aspect of the invention, the medical device includes a topcoat, including a polymer layer. The topcoat may be added by applying a coating layer over the body of the medical device. In this manner, the topcoat can function to control the rate of release of the therapeutic agent from the medical device. In this regard, the thickness of the topcoat layer is selected to provide a desired rate of release of therapeutic agent.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A method for securing an implantable medical device onto a balloon, the method comprising:
    applying a coating to at least a portion of an outer surface of the balloon, the coating comprising a film-forming polymer and at least a first solvent;
    curing the film-forming polymer coating to define a solid, adherent layer on the outer surface of the balloon;
    positioning an implantable medical device on the solid, adherent layer, the implantable medical device including at least one therapeutic agent on at least a portion thereof;
    securing the implantable medical device on the surface of the balloon; and
    applying at least a second solvent to at least a portion of the secured implantable medical device and of the balloon to partially dissolve the solid, adherent layer between an inner surface of the implantable medical device and the outer surface of the balloon to define an adhesive layer disposed between the inner surface of the implantable medical device and the outer surface of the balloon, with reduced leaching of the therapeutic agent from the implantable medical device to the adhesive layer, wherein the at least first solvent is the same as or different from the at least second solvent.

2. The method of claim 1, wherein the implantable medical device is positioned on the surface of the balloon before the coating is dried.

3. The method of claim 1, wherein the implantable medical device is positioned on the surface of the balloon after the coating is dried.

4. The method of claim 1, wherein the film-forming polymer is cured by heating.

5. The method of claim 1, wherein the at least first solvent and at least second solvent are selected from the group consisting of, alcohol, water, ether, alkane, and mixtures thereof.

6. The method of claim 1, wherein at least a portion of the inner surface of the implantable medical device also includes the coating.

7. The method of claim 1, wherein the film-forming polymer is a zwitterionic polymer.

8. The method of claim 7, wherein the film-forming polymer is a phosphorylcholine polymer.

9. The method of claim 7, wherein the film-forming polymer is selected from the group consisting of amino acids, non-ionic hydrophilics, ionic hydrophilics, waxes, hydrophobics, aliphatic polyesters, and any combination thereof.

10. The method of claim 1, wherein the at least first solvent in the coating comprises two solvents.

11. The method of claim 1, wherein the implantable medical device is a stent or graft.

12. The method of claim 1, wherein the at least one therapeutic agent is selected from the group consisting of anti-proliferative agents, anti-platelet agents, anti-inflammatory agents, anti-thrombotic agents and thrombolytic agents.

13. The method of claim 1, wherein the curing step includes removal of the at least first solvent from the coating.

14. The method of claim 13, wherein removal of the at least first solvent occurs by evaporation.

15. The method of claim 1, wherein the film-forming polymer is biodegradable or bioresorbable.

16. A method for securing an implantable medical device onto a balloon, the method comprising:
 applying a coating to at least a portion of an outer surface of a balloon, the coating comprising a film-forming polymer and at least a first solvent;
 positioning an implantable medical device onto the outer surface of the balloon;
 securing the implantable medical device on the surface of the balloon;
 introducing at least a second solvent to at least a portion of the secured implantable medical device and of the balloon after applying the coating to dissolve the film forming polymer between an inner surface of the implantable medical device and the outer surface of the balloon, wherein the at least first solvent is the same as or different from the at least second solvent; and
 curing the film-forming polymer coating to define an adhesive layer between the inner surface of the implantable medical device and the outer surface of the balloon.

17. The method of claim 16, wherein the at least second solvent is spray coated on the surface of the secured implantable medical device and balloon.

18. The method of claim 16, wherein the at least second solvent is introduced as a vapor or mist.

19. The method of claim 16, wherein at least a portion of the inner surface of the implantable medical device includes the coating.

20. The method of claim 16, wherein the film-forming polymer is cross-linkable.

21. The method of claim 20, wherein the curing step includes a step of cross-linking the polymer.

22. The method of claim 16, wherein at least a portion of an outer surface of the implantable medical device includes a therapeutic agent.

\* \* \* \* \*